United States Patent [19]

Lam et al.

[11] Patent Number: 5,188,954
[45] Date of Patent: Feb. 23, 1993

[54] HIGH-AFFINITY HUMAN SEROTONIN UPTAKE SYSTEM

[75] Inventors: Dominic M. Lam; Albert S. Chang, both of The Woodlands, Tex.

[73] Assignee: Baylor College of Medicine, Houston, Tex.

[21] Appl. No.: 274,328

[22] Filed: Nov. 21, 1988

[51] Int. Cl.$^5$ .................... C12N 15/00; C12Q 1/68; C07H 21/00

[52] U.S. Cl. .................... 435/172.3; 435/6; 435/29; 435/69.1; 436/501; 536/23.5; 935/78; 935/88

[58] Field of Search ............... 435/6, 29, 172.3, 69.1; 436/501; 536/27; 935/78, 88

[56] References Cited

U.S. PATENT DOCUMENTS

| | | | |
|---|---|---|---|
| 4,675,285 | 1/1987 | Clark et al. | 435/6 |
| 4,985,352 | 1/1991 | Julius et al. | 435/6 |

OTHER PUBLICATIONS

Lowe et al. (1988), J. of Cell Biol., vol. 106, pp. 51–59.
Old, R. W., et al., "Principles of Gene Manipulation" (1985) 2, pp. 231–234, Blackwell Scientific Publications, London.
Yorek et al., "Synthesis and High Affinity Uptake of Serotonin and Dopamine by Human Y79 Retinoblastoma Cells" (Dec. 1, 1987) *Biological Abstracts*, 84(12) Abstract No. 124514.
Yorek et al., "Amino Acid and Putative Neurotransmitter Transport in Human Y79 Retinoblastoma Cells", *J. Biol. Chem.* (1987), 262(23), pp. 10986–10993.
Allen et al., "Isoproterenol response following transfection of the mouse $\beta_2$-adrenergic receptor gene into Y1 cells", *EMBO Journal* (1988) 7:133–138.
Asano et al., "Rabbit Brain Glucose Transporter Responds to Insulin When Expressed in Insulin-sensitive Chinese Hamster Ovary Cells", *The Journal of Biological Chemistry* (1989) 264:3416–3420.
Blakely et al., "Expression of neurotramsmitter transport from rat brain mRNA in *Xenopus laevis* ooctyes", *Proc. Natl. Acad. Sci. USA* (1988) 85:9846–9850.
Burch and McBride, "Human Gene Expression in Rodent Cells after Uptake of Isolated Metaphase Chromosomes", *Proc. Nat. Acad. Sci. USA* (1975) 72:1797–1801.
Burk et al., "cDNA Cloning, Functional Expression, and mRNA Tissue Distribution of a Third Organellar $Ca^{2+}$ Pump", *The Journal of Biological Chemistry* (1989) 264:18561–18568.
Chang et al., "Characterization of a genetically reconstituted high-affinity system for serotonin transport", *Proc. Natl. Acad. Sci. USA* (1989) 86:9611–9615.
Fraser et al., "Continuous High Density Expression of Human $\beta_2$-Adrenergic Receptors in a Mouse Cell Line Previously Lacking $\beta$-Receptors", *The Journal of Biological Chemistry* (1987) 262:14843–14846.
Hara et al., "Expression of sodium pump activities in BALB/c3T3 cells transfected with cDNA encoding $\alpha_3$-subunits of rat brain $Na^{30}$,$K^+$-ATPase", *FEBS* (1988) 238:27–30.
Jones et al., "Electrophysiological characterization of cloned m1 muscarinic receptors expressed in A9 L cells", *Proc. Natl. Acad. Sci. USA* (1988) 85:4056–4060.
Sardet et al., "Molecular Cloning, Primary Structure, and Expression of the Human Growth Factor-Activatable $Na^+/H^+$ Antiporter", *Cell* (1989) 56:271–280.
Sarthy, "$\gamma$-Aminobutyric acid (GABA) uptake by Xenopus oocytes injected with rat brain mRNA" Molecular Brain Research (1986) 1:97–100.
Takeyasu et al., "Ouabain-sensitive $Na^++K^+$-ATPase Activity Expressed in Mouse L Cells by Transfection with DNA Encoding the $\alpha$-Subunit of an Avian Sodium Pump", The Journal of Biological Chemistry (1988) 263:4347–4354.
Underhill and Flintoff, "Complementation of a Methotrexate Uptake Defect in Chinese Hamster Ovary Cells by DNA-Mediated Gene Transfer", *Molecular and Cellular Biology* (1989) 9:1745–1758.
Dingledine et al., "Amino Acid Receptors and Uptake in the Mammalian Central Nervous System", *CRC Critical Reviews of Neurology* (1988) 4, (1) pp. 1–96.
Blin et al.; "A General Method for Isolation of High Molecular Weight DNA from Eukaryotes"; *Nucleic Acids Research*; vol. 3, No. 9, Sep. 1976, pp. 2303–2308.
Claudio et al.; "Genetic Reconstitution of Functional Acetylcholine Receptor Channels in Mouse Fibroblasts"; *Science*, vol. 238, Dec. 1987, pp. 1688–1694.
Fargin et al; "The Genomic Clone G–21 Which Resembles a Betz-Adrenergic Receptor Sequence Enclodes the 5-Ht Receptor"; *Nature*; vol. 335, Sep. 1988, pp. 358–360.
Frnka et al; "Pharmacological Characteristics of High-Affinity Serotonin Uptake Systems Established Through Gene Transfer"; *The Journal of Pharmacology and Experimental Therapeutics*; vol. 256, No. 2, pp. 734–740.
Julius et al; "Molecular Characterization of a Functional cDNA Encoding the Serotonin Ic Receptor"; *Science*; vol. 241, pp. 558–564.
Kuhn, et al. (1983), *Mol. Biol. Med.* 1:335–352.
Chao, et al. (1986), *Science* 232:518–521.
Greco et al. (1987), *Proc. Natl. Acad. Sci. USA* 84:1565–1569.
Southern and Berg, *J. Molec. Appl. Genet.* (1982) 1:327–341.

Primary Examiner—Amelia B. Yarbrough
Assistant Examiner—Ardin H. Marschel
Attorney, Agent, or Firm—Barbara Rae-Venter; Bertram I. Rowland

[57] ABSTRACT

Non-primate or primate cells are provided comprising a functional human transporter for neurotransmitter uptake. The cells allow for dissection of the mechanism of neurotransmitter transport, as well as screening for agonists and antagonists of the neurotransmitter with respect to its uptake. Methods are provided for producing such cells. Specifically, the cells are transformed with human DNA comprising the gene encoding for the neurotransmitter transporter, whereby this protein(s) is expressed and transported to the membrane and is capable of functioning to transfer the neurotransmitter from the extracellular space intracellularly.

15 Claims, No Drawings

HIGH-AFFINITY HUMAN SEROTONIN UPTAKE SYSTEM

This invention was made with Government support under Grant Nos. EY02423 and EY02608 awarded by the National Institutes of Health/National Eye Institute. The Government has certain rights in this invention.

INTRODUCTION

Technical Field

The technical field of this invention relates to cells having exogenously introduced capability for transmitter-specific high-affinity transport systems and the use of these cells for identifying agonists and antagonists directed at these transport systems.

Background

The inactivation of a neurotransmitter following its release is an essential regulatory step in neurotransmission. For biogenic amine and amino acid neurotransmitters, the inactivation process is achieved mainly by the uptake of the released transmitter from the synaptic cleft, via a transmitter-specific, high-affinity transport system (transporter) present in the presynaptic neuron and/or surrounding glial cells. As the brain has been increasingly investigated, the variety of neurotransmitters and the mechanisms associated with the transmission of signals have proven to be increasingly complicated.

There is increasing interest in being able to investigate the processes involved with neurotransmission in vitro. For a number of reasons, employing neurons in culture has substantial limitations and drawbacks. The shortcomings include inability to establish neuronal cultures that are viable cell lines, homogeneous in neurochemical and neurophysiological composition, well-defined in terms of growth and maintenance requirements, and morphologically and neurochemically stable over time.

It would therefore be of great interest to be able to develop cells which can be grown in culture and could be used for investigating the mechanisms of transmitter-specific transport (uptake) systems, as well as evaluating agonists and antagonists, where the specific system is relatively insulated from other receptors which might be affected by the neurotransmitters under investigation.

Relevant Literature

The expression of exogenously introduced DNA has been described for established cell lines by Wigler et al, Cell (1979) 16:777-785; Kuhn et al, Mol. Biol. Med. (1983) 1:335-352; Chao et al, Science (1986) 232:418-421; and Greco et al, Proc. Natl. Acad. Sci. USA (1987) 84:1565-1569. Transformation of mouse cells with plasmids comprising a viral tranfection system is described by Southern and Berg, J. Mol. Appl. Genet. (1982) 1:327-341.

SUMMARY OF THE INVENTION

Methods are provided for producing non-human cells comprising a functional human transporter capable of transporting a neurotransmitter from the outside to the inside of the cell. The cells are capable of being responsive to agonists and antagonists, as well as ancillary agents associated with the function of the neurotransmitter. Non-primate or primate cells stable in culture are transformed with human genomic DNA for expression of a functional human neurotransmitter transporter.

DESCRIPTION OF THE SPECIFIC EMBODIMENTS

Non-primate or primate cells capable of growing in culture are provided which comprise a functional primate, particularly human, neurotransmitter transporter. Methods are provided for producing these cells, as well as using the cells for investigation of neurotransmitter transport function mechanisms and screening of agonists and antagonists for the neurotransmitter.

The cell cultures of this invention will for the most part be cells derived from non-primate vertebrates, particularly rodentiae, lagomorpha, equine, bovine, porcine, etc., particularly mouse and rat cells. Cells of primate origin may also be used when appropriate. The cells will normally be other than cells associated with the brain, such as neurons, astrocytes, glial cells, or the like. Thus, the cells may be fibroblasts, leukocytes, muscle, bone, stem cells, epithelial cells, endothelial cells, etc. For the most part, the cells will be stable in culture (immortalized), so as to be grown indefinitely and expanded as needed. Cells of particular interest will be those which are easily grown, stably retain the introduced DNA, have a replication system which is not particularly error prone, and do not manifest high rates of endogenous genetic recombination. Cell lines which may find use include mouse L-M fibroblasts, L-TK−fibroblasts, L-929 fibroblasts and 3T3 fibroblasts.

The neurotransmitter transporters which may be introduced into the mouse may include transporters for serotonin, GABA, glycine, dopamine, epinephrine, norepinephrine, acetylcholine, etc.

The exogenous DNA encoding the transporter may be introduced into the host cell in a variety of ways. Conveniently, the host cell may be transformed with human genomic DNA in the presence of DNA which provides for a selection marker. Thus, human genomic DNA may be prepared, as intact chromosomes or as degraded DNA fragments of from about 5 to 100 kbp, and mixed with a plasmid or linear DNA capable of stable maintenance or integration into the genome of the host cell and carrying a selection marker. Conveniently, calcium phosphate precipitation may be employed as described in the literature. For example, the DNA may be dissolved in an appropriate phosphate buffered saline solution, about pH7, and an equal volume of 0.1-0.5M calcium chloride added drop-wise. The precipitate is incubated, followed by adding to the cells and incubating for an extended period of time, usually at least about eight hours and not more than about 24 hours. The cells are separated from the precipitate and then cultured in the presence of the selection agent.

The particular manner of selection is not critical to this invention. For the most part resistance to cytotoxic agents is convenient. Various antibiotics may be employed, but a particularly convenient combination is a neomycin resistant gene APH(3')II with G418, although with appropriate cells, methotrexate with the DHFR gene, or the like may be employed. The selection gene may be associated with a replication system, since the combination of the gene with a replication system generally provides for a larger number of transformed cells which may be selected. Various replication systems are available as derivatives of SV40, bovine papilloma virus, adenovirus, etc. These vectors find ample description in the literature.

Rather than transform with genomic DNA, one may transform with the appropriate transporter gene, where such gene is available. The transformation with genomic DNA avoids the difficulties of identifying mRNA or the genomic sequence in encoding the transporter. If such sequence is available, this sequence may then be used for transformation in accordance with known techniques. It may be desirable to exchange the transcriptional initiation region of such gene with a host transcriptional initiation region, although in some cases this would not be desirable, for example where the human transcriptional region is subject to different conditions for induction from the non-primate transcriptional initiation region and one is interested in the induction mechanism and the effect of compounds on such induction in non-primate host cells. The joining of such gene to a replication system and transformation of the host cells with the resulting plasmids is well known in the literature and the subject gene could be introduced into a plasmid used as the marker plasmid, so that the host would be simultaneously transformed with the marker and the subject receptor gene. Selection would follow in the same way as selection occurred for co-transfection of a marker plasmid and genomic DNA.

Colonies are then selected based on resistance to the cytotoxic agent, followed by uptake of labelled, normally radioactive-labelled, neurotransmitter. After contacting the cell colonies with the labelled neurotransmitter, and incubating for sufficient time, usually from about 0.5 to about two hours at physiological temperature, the cells are then thoroughly washed to remove any extracellular neurotransmitter. The intracellular presence of the neurotransmitter may then be determined by virtue of the label. Conveniently, a radiolabel is employed. Desirably, a second assay is performed which allows for normalization of the results from different colonies, to correct for differences in the number of cells or levels of expression in individual cells. It has been found that an assay for alkaline phosphatase may be used as the normalizing expression product. Alternatively, protein quantitation via the BCA method can also afford normalization of a large number of samples simultaneously.

In order to ensure that the neurotransmitter uptake is related to expression of the human transporter, the cell colonies may be further screened to demonstrate that the serotonin uptake is dependent upon conditions and ancillary compounds associated with the in vivo neurotransmitter uptake. For example, with serotonin, the uptake of serotonin is sodium ion dependent as well as temperature dependent, so that a showing of temperature and sodium dependence would be indicative of serotonin uptake by virtu of the presence of the transporter. In addition, one may employ agonists and antagonists, such as imipramine and demonstrate that the uptake is sensitive to the presence of agonists and is inhibited by antagonists. Furthermore, rigorous kinetic measurements can be employed to establish the affinity and capacity of the neurotransmitter uptake system as being in agreement with high-affinity uptake systems detected in vivo.

Once the cells have been identified as being specific for a particular neurotransmitter and that transport is dependent upon a functional neurotransmitter transporter which is sensitive to the same agents and conditions associated with the human neurotransmitter transporter present in humans, the cells may then be used in a wide variety of ways. The cells may be used in research for investigating the mechanism of the neurotransmitter interacting with its transporter. One could further transform the host cell with other human genes(s) to determine what the effect of the expression of the other human gene has on the functioning of the neurotransmitter. In this way, one may be able to determine the presence of associations which may have specific effects on the functioning of the neurotransmitter transporter. One may relate changes in polarity of the cell, by identifying certain channels associated with the functioning of the cell. In addition, one may change the ionic strength in the medium in which the cell is grown or the concentration of a specific cation to investigate the various effects of the inorganic salts.

Of particular interest is the use of the transformed host cells for screening compounds for agonist or antagonist activity. Thus, by measuring the amount of neurotransmitter which is introduced into the host cells in the presence or absence of the investigatory or candidate compound, one can evaluate the role of the compound. Agonists will be distinguished from antagonists, where transport of the neurotransmitter is associated with a specific function which is observable with the cell. Where no such specific function occurs, then the compounds may be further screened with neurons or brain tissue to determine whether the compound is an agonist or antagonist. Thus, the subject transformed host cells provide for a rapid and efficient screening for compounds which can competitively bind the human neurotransmitter transporter, so as to prevent the binding or transport (uptake) of the natural neurotransmitter.

EXPERIMENTAL

The following examples are offered by way of illustration and not by way of limitation.

METHOD: Mouse L-M fibroblast cells (ATCC CCL 1.2) were cultured in Dulbecco's Modified Eagle Medium (GIBCO) supplemented with 10% defined Bovine Serum (Hyclone, Inc.) and 1% penicillin/streptomycin (GIBCO). Cells were preplated in 100 mm culture dish such that by the time of transfection the cell number would be about $10^6$. Human genomic DNA (50 $\mu$g) and pSV2neo (Southern and Berg, supra) (0.1 $\mu$g) were combined in 280 mM NaCl, 10 mM KCl, 1.5 mM $Na_2HPO_4$, 10 mM glucose, 50 mM HEPES, pH 7.05, and an equal volume of 0.25M $CaCl_2$ was added dropwise. The precipitate was kept at room temperature for approximately 30 min before being mixed with culture medium and added to L-M cells for 16 hrs. The precipitate-mixture was then removed and the cells replated into 96-well plates to be cultured in the presence of G418 (GIBCO; 400 $\mu$g/ML) until transfectant colonies were well-established. Typically, each well contained 3-5 colonies following G418-selection. Each well containing transfectant(s) was then trypsinized and replated into separate sets for both assays and cell-stocks. During the initial screening, the entire bank of transfectants were assayed for [$^3$H]-serotonin uptake. To perform the uptake assay on 96-well plates, culture medium of each well was first removed, the cells rinsed twice with oxygenated Ringer's solution (128 mM NaCl, 5.2 mM KCl, 2.1 mM $MgSO_4$, 5 mM glucose, 10 mM HEPES, pH 7.4, supplemented with 0.5 mM ascorbate, 0.5 mM pargyline) and then incubated with 50 $\mu$l of Ringer's solution plus 0.1 μM [³H]-serotonin for 40 min at 37° C. The incubation mixture was then removed and each well washed three times before adding 50 μl of alkaline phosphatase buffer: 100 mM Tris, pH 9.5, 100 mM NaCl, 10 mM/MgCl₂, 20 μg/ml saponin, 3.2 mg/ml p-nitrophenyl phosphate. This assay was employed as a rapid and convenient measure of relative cell number for each well and served as a normalizing measure to expedite data analyses. The phosphatase reaction was conducted for 1-2 hrs. at 37° C., and terminated with addition of 100 μl 1% SDS to each well. The extent of the phosphatase reaction for each well was measured at 405 nm with an automated ELISA reader. The [³H]-content of each well was then determined by scintillation counting. The data for all the assayed wells were then plotted, the cpm level of each well versus its corresponding phosphatase reading. The majority of the data points clustered together in a "main cluster" represented by a linear positive slope. In contrast, the rare high respondents in the assay can be identified as relatively high points above the cluster. The wells containing the high respondents were then expanded from stock plates and rescreened to ensure consistency of high responses. Additionally, these wells were also tested with imipramine, a known blocker of serotonin uptake. For such inhibition assays, the cells in each well were first preincubated with Ringer's solution plus 10 μM imipramine at 37° C. for 10 min. [³H]-serotonin was then added into each well to reach 0.1 μM and the assay conducted at 37° C. for an additional 40 min. Wells demonstrating both high levels of [³H]-serotonin and imipramine antagonism during the second screening were then used to generate single-cell cultures. The single-cell clones that subsequently arose were once again tested for both extent of [³H]-serotonin uptake, as compared with L-M cells, and imipramine antagonism. In this manner, strain L-S1 was identified as one of the monoclones possessing the desired features.

Uptake assays of [³H]-serotonin by L-S1 and L-M were performed with Ringer's solution of varying ionic compositions or different assay temperatures. All assays were performed with 0.1 μM [³H]-serotonin for 40 min. For Na⁺-dependence, the uptake level of LS1 with normal Ringer's solution ("+Na") was set at 100% and used to normalize the uptake levels of L-S1 and L-M assayed in the absence of Na+. Sucrose-supplementation was used to obtain Na+-deficient Ringers ("−Na") by using 256 mM of sucrose to isoosmotically replace 128 mM of NaCl in making Ringer's solution while all other components remained invariant. Similarly, Ca²⁺-dependence was tested by setting L-S1 uptake levels in normal Ringer's solution ("Na+Ca") at 100% and compared with uptake levels in Ringer's solution wherein Ca²⁺ was replaced by Co²⁺('-'Na+Co") or ("Na+Mg"). L-M cells were assayed in parallel. Temperature-dependence was tested by performing the uptake assay at both 37° C. and 0° C. (on ice). Prior to each assay, the cells were first allowed to equilibrate to the desired temperature for 10 min. L-S1 assayed at 37° C. was set as 100% level, against which data obtained for 0° C. were normalized. All data were first converted to cpm/mg protein prior to normalization against L-S1 uptake levels, and tabulated for illustration in Table I.

The specificity of [³H]-serotonin uptake by L-S1 and L-M cells was determined as follows. L-S1 and L-M cells were preplated into 96-well culture plates and assayed by incubating each well with oxygenated Ringer's solution plus 0.1 μM of [³H]-serotonin and without or with a competing, unlabelled ligand. The repertoire of competing ligands are as follows: serotonin (5HT); imipramine (IMIP); dopamine (DA); γ-aminobutyric acid; tryptophan; tyrosine; and phenylalanine. Each competing ligand was added to the assay to a final concentration of 10μM. The assays were conducted for 40 min at 37° C. Following several washes at room temperature with excess Ringer's solution, the cells were lysed with 1% SDS and a fraction of each well-lysate added to ACS scintillant (Amersham Co.) for counting. The remaining lysate of each well was used for protein content determination using the modified Lowry's method or the BCA method. The extent of [³H]-accumulation in each well was then normalized by its protein content and expressed as "cpm/mg protein" for comparison pruposes.

TABLE I

| ION AND TEMPERATURE DEPENDENCES OF [³H]-SEROTONIN UPTAKE BY L-S1 | | |
|---|---|---|
| | L-S1 (%) | L-M (%) |
| Sodium: +Na | 100.00 | 18.90 ± 2.07 |
| −Na | 12.37 ± 1.66 | 11.46 ± 1.28 |
| Calcium: Na + Ca | 100.00 | 17.30 ± 1.70 |
| Na + Co | 97.64 ± 10.62 | 16.12 ± 1.44 |
| Na + Mg | 98.56 ± 10.09 | 18.48 ± 1.57 |
| Temp.: 37° C. | 100.00 | 11.70 ± 1.04 |
| 0° C. | 2.77 ± 0.29 | 1.36 ± 0.07 |

The observed results showed that the untransformed host maintained a relatively constant and low level of serotonin uptake. By contrast, with the exception of the presence of IMIP and 5HT, the level of serotonin uptake remained about the same or slightly greater with the various competing ligands. Thus, none of the unrelated ligands had a significant effect on the specific uptake of serotonin by the L-S1 cell.

Kinetic analyses of [³H]-serotonin uptake by L-S1 were performed. Uptake assays were performed on L-S1 and L-M with [³H]-serotonin at the following concentrations (M): $5 \times 10^{-5}$, $2 \times 10^{-5}$, $10^{-5}$, $5 \times 10^{-6}$, $2 \times 10^{-6}$, $10^{-6}$, $5 \times 10^{-7}$, $2 \times 10^{-7}$. As control, L-S1 was also assayed at the above-given concentrations plus 100-fold molar excess of unlabelled serotonin. In each kinetic experiment, identical sets of cells were assayed with the concentration series listed above at both 37° C. and 0° C. All assays were for 10 min, because the velocity of [³H]-serotonin uptake by L-S1 is linear within that time frame. The measured cpm levels were each converted to mole-equivalents of serotonin based upon the specific activity of the ³H-label, followed by normalization by both protein content and length of assay. Such values (expressed as pmol/mg/min) obtained at 37° C. were subtracted by corresponding ones obtained at 0° C. resulting in the specific uptake velocity of each cell-type at a given concentration of radiolabelled serotonin in the absence or presence of excess unlabelled serotonin.

A Michaelis-Menton plot of specific uptake velocity (V) versus [³H]-serotonin concentration (S) for both L-S1 and L-M, was made. Also, the data was analyzed by a Lineweaver-Burk plot by plotting the inverse of the velocity values (1/V) against the inverse of the concentration values (1/S). Data for L-S1, L-S1 with excess unlabelled serotonin and L-M were each fitted to a straight line by linear regression, and in each case the correlation coefficient was 0.99 or higher. With the equation obtained for L-S1 in Lineweaver-Burk transformation, both its x- and y-intercepts were extrapolated and inverted to calculate L-S1's $K_m$ and $V_{max}$ for serotonin uptake.

The kinetic analyses showed that the serotonin uptake by L-S1 is a saturable process, in contrast to the L-M cell. Likewise, the Lineweaver-Burk plot of L-S1 yielded a straight line with a discernible negative abscissa-intercept, while L-M cells did not. The abscissa-inordinate-intercepts of L-S1 yielded an apparent $K_m$ of $0.39 \pm 0.096$ μM and a $V_{max}$ of $2.14 \pm 0.55$ pmol/min/mg protein for serotonin uptake system. These values are comparable with those of high-affinity neuronal serotonin uptake systems previously reported (Osborne and Hamon, Eds. *Neuronal Serotonin*, John Wiley and Sons, New York (1988), support the fact that L-S1 accumulates serotonin by high-affinity mechanisms. This is further supported by the fact that when L-S1 was incubated with Ringer's solution containing the double-reciprocal plot of L-S1's response shifted to resemble that of L-M cell.

Genomic blotting analyses with a human Alu sequence probe indicated that L-S1 integrated human DNA, as manifested by discrete hybridizing DNA fragments within an extensive smear pattern. In contrast, no discernible hybridizing signal was observed with L-M. By comparison of the overall hybridizing strength observed for L-S1 DNA with that of known quantities of human genomic DNA, a conservative estimate is that L-S1 contains over $10^6$ bps of stably integrated human DNA.

To further demonstrate that the radioactivity measured in L-S1 represented transport of tritiated-serotonin into these cells, (1) autoradiography of these cells following incubation with tritiated serotonin showed that most of the radioactivity was inside the cells rather than binding on the surface; and (2) when analyzed by reverse-phase HPLC, over 90% of the radioactivity inside these cells co-migrated with tritiated serotonin.

It is evident from the above results, that novel methods and compositions are provided for studying neurotransmitter transport in cell culture. Thus, an important new tool is provided for dissecting the mechanism of neurotransmitter transport, while also allowing for rapid screening of a large number of compounds for their ability to bind to the receptor and be transported intracellularly or compete with compounds bound by the receptor.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An in-vitro composition consisting essentially of non-human mammalian cells capable of being grown in culture and characterized by:
    comprising a human genome fragment comprising a DNA sequence encoding a serotonin transporter.
2. A composition according to claim 1, wherein said cells are cells of the genus rodentiae.
3. A composition according to claim 1, wherein said cells are other than neuronal cells.
4. A composition according to claim 1, wherein said cells are obtained by a method which comprises transforming non-human mammalian cells with human genomic fragments and a marker gene; and
    selecting for the presence of said marker and a functional neurotransmitter transporter.
5. An in-vitro composition consisting essentially of non-primate mammalian cells capable of being grown in culture and characterized by:
    comprising a human DNA sequence encoding a serotonin transporter.
6. A composition according to claim 5, wherein said cells are obtained by a method which comprises transforming non-primate mammalian cells with human genomic fragments and a marker gene; and
    selecting for the presence of said marker and a functional serotonin transporter.
7. A composition according to claim 5, wherein said cells are mouse fibroblast cells.
8. A composition according to claim 7, wherein said cells further comprise a cytotoxic agent resistance gene and are resistant to said cytotoxic agent.
9. An in-vitro consisting essentially of comprising:
    transgenic mouse fibroblast cells characterized as (1) capable of being grown in culture; and (2) containing integrated into their genome a human genomic fragment comprising a DNA sequence encoding a serotonin transporter.
10. An in-vitro culture transgenic mouse fibroblast cells containing integrated into their genome a human genomic fragment comprising a DNA sequence encoding a serotonin transporter.
11. A culture of transgenic mouse cells containing integrated into their genome a human genomic fragment comprising a DNA sequence encoding a transporter produced by the method of (a) transforming mouse cells with said human genomic DNA by calcium phosphate precipitation and selecting for transfectants by means of a selection marker on a cotransfected plasmid.
12. The culture according to claim 11, wherein said mouse cells are fibroblast cells.
13. The culture according to claim 12, wherein said fibroblast cells are L-M cells.
14. An in-vitro culture of transgenic mouse fibroblast cells capable of transporting serotonin as a result of transformation with a human genomic fragment comprising a DNA sequence encoding a serotonin transporter.
15. The culture according to claim 14, wherein said transporting is sodium ion and temperature dependent and is blocked by imipramine.

* * * * *

UNITED STATES PATENT AND TRADEMARK OFFICE
CERTIFICATE OF CORRECTION

PATENT NO. : 5,188,954
DATED : February 23, 1993
INVENTOR(S) : Dominic M. Lam and Albert S. Chang It is certified that error appears in the above-indentified patent and that said Letters Patent is hereby corrected as shown below:

Column 3, line 57, change "virtu" to -- virtue --.

Column 5, line 48, change "isoosmotically" to -- iso-osmotically --.

Column 5, line 54-55, change "$Co^{2+}('-'Na+Co")$ or ("$Na+Mg$")" to -- $Co^{2+}("Na+Co")$ or $Mg^{2+}$ ("$Na+Mg$") --.

Column 7, lines 8-9, change "abscissa-inordinate-intercepts" to -- abscissa-ordinate-intercepts --.

Column 7, line 18, after "containing" insert -- tritiated-serotonin and excess unlabelled serotonin, --.

Column 8, line 42, change "A culture" to -- An _in-vitro_ culture --.

Column 8, line 44, before "transporter" add -- serotonin --.

Signed and Sealed this

Twenty-third Day of May, 1995

Attest:

Attesting Officer

BRUCE LEHMAN

Commissioner of Patents and Trademarks